United States Patent
Chu et al.

(10) Patent No.: US 6,766,800 B2
(45) Date of Patent: Jul. 27, 2004

(54) PRESSURE REGULATING VALVE FOR USE IN CONTINUOUS POSITIVE AIRWAY PRESSURE DEVICES

(75) Inventors: Edmond Chu, San Diego, CA (US); Tim Quinn, Carlsbad, CA (US); Larry Murdock, Alta Loma, CA (US); Hung Tran, Yorba Linda, CA (US)

(73) Assignee: Sensormedics Corporation, Yorba Linda, CA (US)

( * ) Notice: Subject to any disclaimer, the term of this patent is extended or adjusted under 35 U.S.C. 154(b) by 0 days.

(21) Appl. No.: 10/231,859

(22) Filed: Aug. 30, 2002

(65) Prior Publication Data

US 2004/0040563 A1 Mar. 4, 2004

(51) Int. Cl.$^7$ .......................... A61M 16/00; A62B 9/02
(52) U.S. Cl. .......................... 128/205.24; 128/205.25; 128/207.12; 128/206.28; 128/206.21; 128/204.18; 128/204.23; 137/601.2
(58) Field of Search ....................... 128/205.24, 205.25, 128/207.12, 207.13, 206.15, 205.16, 200.22, 206.28, 206.21, 206.18, 204.18, 204.23; 137/601.2, 512.1

(56) References Cited

U.S. PATENT DOCUMENTS

| | | | |
|---|---|---|---|
| 4,655,213 A | 4/1987 | Rapoport et al. ...... | 128/205.25 |
| 4,926,855 A * | 5/1990 | Hellquist et al. ...... | 128/201.28 |
| 5,065,756 A | 11/1991 | Rapoport ............... | 128/204.18 |
| 5,109,840 A * | 5/1992 | Daleiden ............... | 128/205.13 |
| 5,134,995 A | 8/1992 | Gruenke et al. ....... | 128/204.23 |
| RE35,339 E | 10/1996 | Rapoport ............... | 128/204.18 |
| 5,694,923 A | 12/1997 | Hete et al. ............. | 128/204.18 |
| 5,730,122 A * | 3/1998 | Lurie ..................... | 128/207.12 |
| 5,878,743 A | 3/1999 | Zdrojkowski et al. . | 128/204.23 |
| 6,006,748 A * | 12/1999 | Hollis ................... | 128/205.24 |
| 6,102,038 A * | 8/2000 | DeVries ................. | 128/205.24 |
| 6,182,657 B1 | 2/2001 | Brydon et al. ......... | 128/205.24 |
| 6,189,532 B1 * | 2/2001 | Hely et al. ............. | 128/205.24 |
| 6,253,764 B1 | 7/2001 | Calluaud ............... | 128/204.18 |
| 6,343,603 B1 | 2/2002 | Tuck et al. ............ | 128/205.24 |
| 6,371,117 B1 | 4/2002 | Lindqvist et al. ...... | 128/207.12 |

OTHER PUBLICATIONS

Advanced Solutions in Non–Invasive Acute Respiratory Care, "SealFlex Multi–Strap Mask," caradyne Lit. 5287 Rev. 8, 9/00, p. 0344.

The CPAP Machine, www.sleepdesk.co.uk/apnea4.htm, printed Apr. 10, 2002, 2 pages.

(List continued on next page.)

Primary Examiner—Henry Bennett
Assistant Examiner—Mital Patel
(74) Attorney, Agent, or Firm—Sidley Austin Brown & Wood

(57) ABSTRACT

A valve for use in continuous positive airway pressure (CPAP) devices includes a valve body that is disposed at or between the patient mask and the source of positive airway pressure. The valve body includes first and second exhaust paths for exhausting gas from the mask. A floating valve seat is disposed in the valve body and is moveable between first and second positions. A moveable spring-biased piston is releasably engaged with the floating valve seat. When the floating valve seat is in the first position, the moveable spring-biased piston is disengaged from the valve seat and gas travels out the first exhaust flowpath. When the floating valve seat is in the second position, the moveable spring-biased piston is engaged with the valve seat and gas travels out the second exhaust flowpath. The valve provides substantially constant positive airway pressure to the patient at pressures above the threshold pressure level of the valve. When the pressure drops below the threshold value, the valve opens a secondary flowpath in the valve.

14 Claims, 3 Drawing Sheets

OTHER PUBLICATIONS

The CPAP Store, "CPAP, Bi–Level Equipment and Supplies for Sleep Apnea at Super Discount Prices," "Sullivan® Mirage Mask System," GoldSeal Gel Mask with Headgear, "Tubing Insulation Sleeve," www.cpapman.com/supplie2.htm; printed Apr. 10, 2002, 3 pages.

The CPAP Store, "ResMed (Sullivan) Equipment," "SullivanAutoSet T," "ResMed S6 Lightweight," "Sullivan Comfort," "ResMed Enhanced VPAP II," "Ultra Mirage Mask," Mirage Nasal Mask, "Mirage Full Face Mask Series 2," "SwingArm™", www.cpapman.com/resmed.html, printed Apr. 10, 2002, 18 pages.

ResMed Innovators in Sleep and Respiratory, "Ultra Mirage Mask," www.resmed.com/us/, printed Apr. 10, 2002, 3 pages.

* cited by examiner

PRESSURE REGULATING VALVE FOR USE IN CONTINUOUS POSITIVE AIRWAY PRESSURE DEVICES

FIELD OF THE INVENTION

The field of the invention relates generally to Continuous Positive Airway Pressure (CPAP) devices. More specifically, the field of the invention relates to pressure regulating valves used in connection with CPAP devices.

BACKGROUND OF THE INVENTION

CPAP devices are effective in treating obstructive sleep apnea. In all CPAP devices a mask (which may be nose mask, mouth mask, or face mask) is connected to a source of pressurized gas (typically air) via a flexible tubing. The source of gas is typically a flow generator that uses a turbine or blower that is connected to an electrically powered motor. During operation, the mask is then worn by the patient and the flow generator is powered to produce a positive mask pressure within the range of about 3 cm $H_2O$ to about 20 cm $H_2O$. The positive applied pressure eliminates the negative pressure within the pharyngeal lumen thereby acting as a pneumatic splint to maintain the patient's airway patency.

In CPAP therapy, the pressure of the delivered gas is carefully chosen by the sleep therapist or other qualified health care professional to maintain adequate airway pressure (i.e., maintain an open airway). This pressure can be different for each patient. It is therefore extremely important to accurately maintain the prescribed gas pressure during the administration of CPAP to the patient. If the pressure falls below the optimal prescribed pressure, the patient will often have an increased number of apneic or hyponeic episodes. In contrast, if the pressure rises above the optimal prescribed pressure, the patient will often times experience discomfort because of the increased work of breathing needed to overcome the high positive pressure.

In prior art CPAP devices, the pressurized gas is typically provided by a flow generator consisting of an electrically powered motor that is coupled to a turbine or impeller. Holes are incorporated into the patient mask to ensure a continuous flow of air thereby minimizing the rebreathing of exhaled gas by the patient. During inhalation, the flow rate of the air within the patient breathing circuit increases, which, in turn causes a commensurate decrease at the mask end of the breathing circuit. This decrease in pressure is below the optimal prescribed pressure. Conversely, during exhalation, the pressure experienced by the patient increases to a level that is higher than the prescribed optimal pressure.

Some prior art CPAP devices attempt to correct these transient pressure fluctuations during patient inhalation and exhalation by adjusting the speed of the motor that powers the flow generator. Typically, one or more pressure sensors are located within the patient breathing circuit and connected, in a feedback arrangement, with a controller that controls the speed of the motor powering the flow generator. When a pressure decrease is detected by the pressure sensor, the controller increases the speed of the motor to increase the flow rate within the breathing circuit (and thus increase the pressure therein). Similarly, when a pressure increase is detected by the pressure sensor, the controller slows the rotational speed of the flow generator motor to compensate for the pressure increase.

Unfortunately, this feedback arrangement has its limitations. Due to the relatively high inertia of the motor and the turbine/impeller, it is extremely difficult to develop a compensation system that has a rapid response time that can compensate for the transient pressure increases/decreases caused by the active breathing of a patient. The desire to improve the response time often results in oscillations in the output pressure of the flow generator. A survey of the performance of commonly used CPAP devices indicates that pressure fluctuations within +/–2 cm $H_2O$ or higher can result within physiologic flow rates (i.e., between about 50 liters/minute to about 60 liters/minute).

U.S. Pat. No. 4,655,213 issued to Rapport et al. discloses a method and apparatus for the treatment of obstructive sleep apnea. The apparatus includes a nose mask assembly that is adapted to be sealed over the nose of a patient. The mask has an inlet for supplying continuous positive pressure of air to the mask. The mask also includes a threshold valve that releases air from the mask. While the apparatus of Rapport et al. is useful for relatively high pressures, the valve mechanism has serious limitations at low pressures. For example, in the Rapport et al. device, when the output pressure of the compressor falls below the threshold pressure of the valve, when the patient exhales, the transient increase in pressure is not enough to open the threshold valve. Consequently, the patient exhales $CO_2$ laden gas into the breathing circuit. On the next inhalation, the patient re-breathes this exhaled gas. Serious health problems can result if this expired gas is not vented to atmosphere immediately upon exhalation.

Consequently, there is a need for a device and method that will deliver a prescribed air pressure to a patient receiving CPAP therapy. The device and method will be able to provide a substantially constant positive airway pressure to the patient and compensate for the transient pressure fluctuations associated with inhalation and exhalation. In addition, the device and method will permit the immediate evacuation of exhaled gases, even at very low pressures.

SUMMARY OF THE INVENTION

In a first aspect of the invention a valve for used in a CPAP device is disposed at a patient mask or, alternatively, at a location between the patient mask and the source of positive airway pressure. The valve includes a valve body having a first exhaust flowpath and a second exhaust flowpath. A floating valve seat is disposed in the valve body and is moveable between a first position and a second position. A moveable spring-biased piston provided in the valve and is releasably engaged with the floating valve seat. When the floating valve seat is in the first position, the moveable spring-biased piston is disengaged from the floating valve seat and gas travels out of the first exhaust flowpath. When the floating valve seat is in the second position, the moveable spring-biased piston is engaged with the floating valve seat and gas travels out the second exhaust flowpath.

In a second aspect of the invention, a mask is connectable to a source of positive airway pressure. A valve is disposed in the mask for controllably releasing gas therefrom to produce a substantially constant pressure inside the mask. The valve includes a valve body having a first exhaust flowpath and a second exhaust flowpath. A floating valve seat is disposed in the valve body and is moveable between a first position and a second position. A moveable spring-biased piston provided in the valve and is releasably engaged with the floating valve seat. When the floating valve seat is in the first position, the moveable spring-biased piston is disengaged from the floating valve seat and gas travels out of the first exhaust flowpath. When the floating valve seat is in the second position, the moveable spring-biased piston is engaged with the floating valve seat and gas travels out the second exhaust flowpath.

In a third, separate aspect of the invention, a method of delivering continuous positive airway pressure to a patient includes the steps of providing a source of positive airway pressure, providing a mask that connects the patient to the source of positive airway pressure, the mask including a valve therein for controllably releasing gas from the mask so as to produce a substantially constant pressure within the mask. The valve in the mask includes first and second exhaust flowpaths, wherein gas is released through the first exhaust flowpath in the valve when the pressure inside the mask exceeds the a threshold value and wherein gas is released through the second exhaust flowpath when the pressure inside the mask falls below the threshold value.

It is an object of the invention to provide a valve for use in CPAP devices that produces substantially constant pressure in the mask worn by a patient. It is a further object of the invention to provide a valve with a fail-safe feature that allows the patient to inhale and exhale atmospheric gas when the pressure within the mask worn by the patient falls below a threshold value. Additional objects of the invention are described in more detail below.

DETAILED DESCRIPTION OF THE PREFERRED EMBODIMENTS

Figure 1:
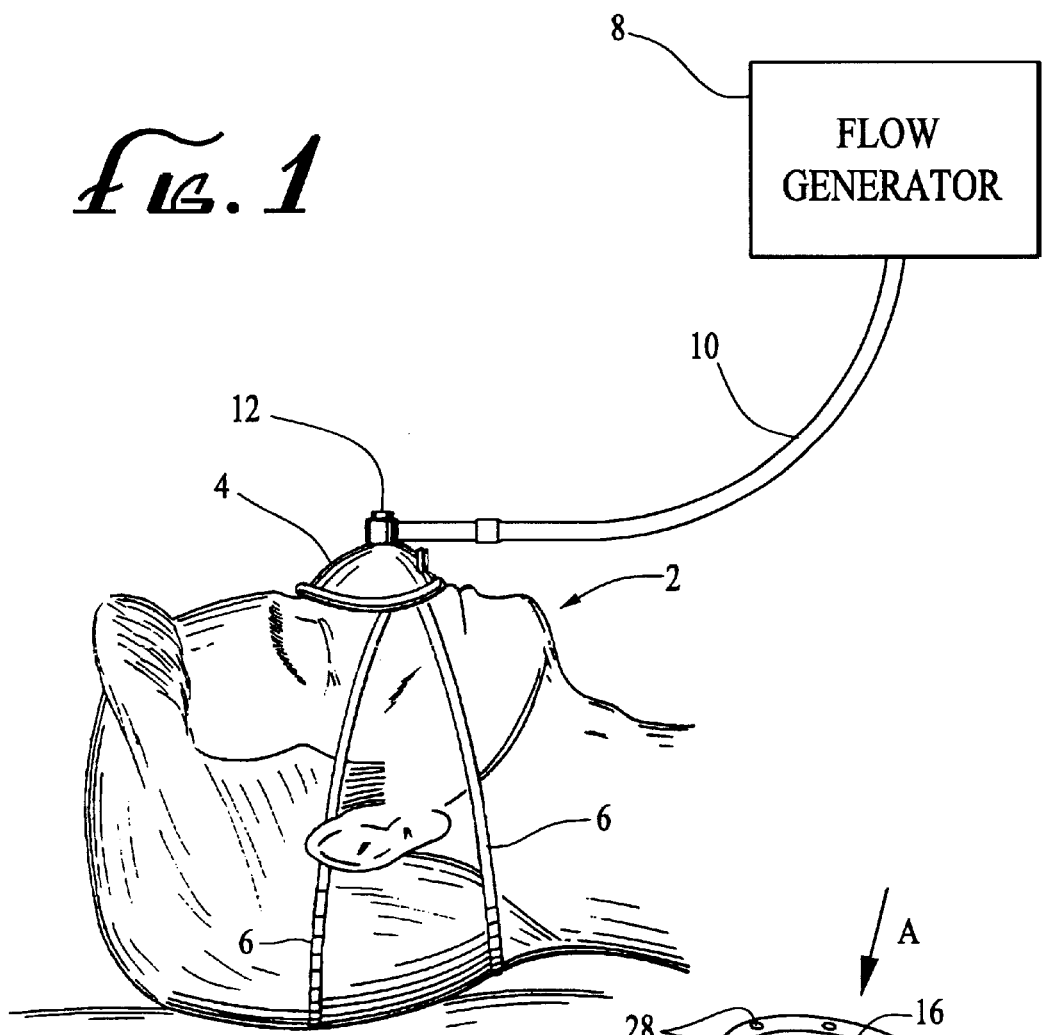
FIG. 1 illustrates a patient wearing a mask according to one preferred aspect of the invention that is connected to a source of positive airway pressure, which in this case, is a flow generator.

FIG. 1 illustrates a patient 2 wearing a mask 4 that is secured to the head of the patient 2 using elastic straps 6. The straps 6 aid in forming an air-tight seal between the patient's face and the mask 4. While FIG. 1 explicitly shows a nasal mask 4, it should be understood that other types of masks 4 such as mouth masks or full face masks may also be used. The mask 4 is connected to a source of positive airway pressure 8 via flexible tubing 10. The source of positive airway pressure 8 can be any number of devices. Typically, the source of positive airway pressure 8 is a flow generator. Flow generators produce a pressurized flow of air by using an electrical motor that is coupled to a turbine or impeller that supplies airflow through the flexible tubing 10.

Alternatively, the source of positive airway pressure 8 may include a compressed gas that is stored within, for example, a pressurized cylinder. The compressed gas may also be delivered via a dedicated wall line, such as those found in hospitals and medical clinics. All that is required for the source of positive airway pressure 8 is that the device be able to supply gas to the patient at physiologic flow rates. In some instances, the source of positive airway pressure 8 may be coupled to a separate gas such as enriched oxygen, that aids in treating patients suffering from chronic obstructive pulmonary diseases.

The mask 4 in FIG. 1 has a valve 12 that serves several functions. First, the valve 12 maintains a substantially constant pressure at the mask 4 when the pressure supplied by the source of positive airway pressure 8 is above the threshold pressure (discussed in detail below) of the valve 12. The term "substantially constant" is meant to indicate that pressure fluctuations in the mask 4 are less than about +/−1 cm $H_2O$. The valve 12 also has a fail-safe feature in that, at low pressures (i.e., pressures below the threshold pressure of the valve 12), the exhaust gas flowpath through the valve 12 changes to allow exhaled gas to quickly exit from the mask 4. In this regard, the valve 12 prevents the patient 2 from re-breathing his or her own exhaled gas. This is particularly important because it eliminates the possibility of asphyxiation should the source of positive airway pressure 8 stop delivering gas to the patient 2.

While FIG. 1 shows the valve 12 located in the mask 4 (the preferred location), the valve 12 can also be disposed at any location between the mask 4 and the source of positive airway pressure 8.

Figure 2:
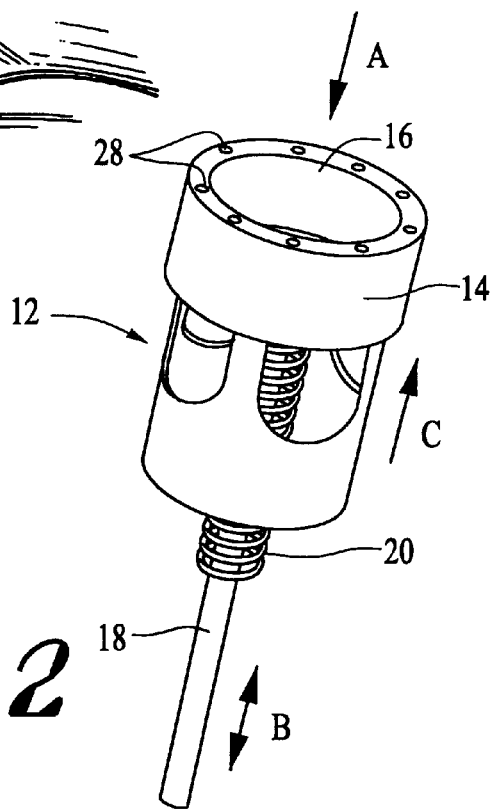
FIG. 2 illustrates an isometric view of the valve according to a preferred aspect of the invention.

FIG. 2 shows one preferred embodiment of the valve 12. The valve 12 includes a valve body 14 that has a central lumen 16 through which gases flow in the direction of arrow A when the pressure in the mask 4 exceeds the threshold pressure of the valve 12. The valve body 14 holds a moveable piston 18 that is translatable in the directions of arrow B. The piston 18 is spring-biased toward the valve body 14 (in the direction of arrow C) by a spring 20. In this embodiment, the spring 20 is under compression to bias the piston 18 toward the valve body 14. It should be understood, however, that the spring 20 may be held in tension in an alternative construction to bias the piston 18 toward the valve body 14.

Figure 3:
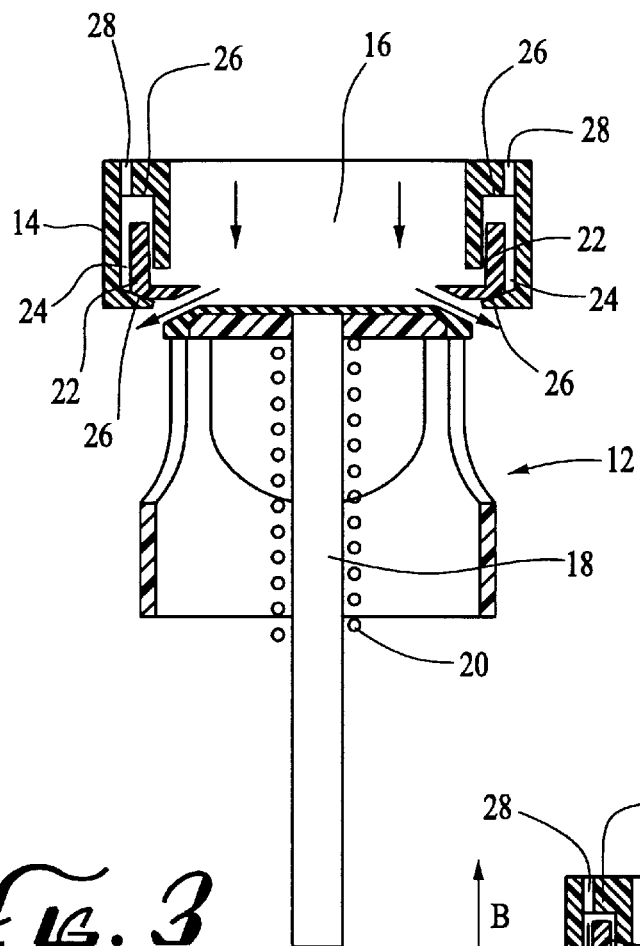
FIG. 3 shows a cross-sectional view of the valve. In this view the pressure from the flow generator exceeds the threshold pressure of the valve, causing exhausting of gas through a first flowpath.

Referring now to FIG. 3, valve body 14 includes a floating valve seat 22, against which, the piston 18 is held when the pressure in the mask 4 is below the threshold pressure of the valve 12. The floating valve seat 22 is disposed within a recessed area 24 of the valve body 14 and is movable in the directions of arrow B between first and second positions, depending on the pressure inside the mask 4 (or within the flexible tubing 10 if the valve 12 is disposed between the mask 4 and the source of positive airway pressure 8). A valve seat stop 26 on either end of the floating valve seat 22 limits the extent of movement of the floating valve seat 22. Referring to FIG. 2, the valve body 14 includes a plurality of ports 28 that allow gases to communicate with the recessed area 24 holding the floating valve seat 22. Depending on the position of the floating valve seat 22, which is described in more detail below, gas is either prevented or permitted to exhaust from the valve 12 via the ports 28.

FIG. 3 illustrates a cross-sectional view of the valve 12 shown in FIG. 2. In FIG. 3, the valve 12 is experiencing a pressure that exceeds the threshold value of the valve 12. In this respect, the pressure of the gas entering the ports 28 pushes against the floating valve seat 22 and moves the floating valve seat 22 to a first position. In this first position, which is shown in FIG. 3, the floating valve seat 22 is pushed against one of the valve seat stops 26. When the floating valve seat 22 is in this first position, gas cannot exit the valve 12 via the ports 28 and recessed area 24.

With respect to the lumen 16 of the valve 12, the pressure of the gas contained therein pushes on the piston 18 and causes the piston 18 to lift away from the surface of the floating valve seat 22. A gap is formed between the piston 18 and the floating valve seat 22 through which gases pass freely. When the pressure is above the threshold value of the valve 12, gas is continuously exhausted through this gap. This gap forms a first exhaust flowpath of the valve 12. The piston 18 is preferably made from a light weight material such as, for example, polycarbonate. In addition, the spring 20 preferably has a low spring constant. By using a spring 20 with a low spring constant, the displacement of the piston 18 will be relatively large for a small change in pressure, thereby ensuring good pressure regulation. These two features allow the valve 12 to achieve substantially constant pressure within the mask 4.

Still referring to FIG. 3, the valve 12 maintains a substantially constant pressure within the mask 4 as follows. When the pressure within the mask 4 is above the threshold value for the valve 12, the piston 18 is lifted off of the floating valve seat 22. When the pressure in the mask 4 starts to rise, for example, when the patient 2 exhales, the piston 18 moves further away from the floating valve seat 22, thereby exhausting additional gas and, therefore, excess pressure from the valve 12.

Conversely, when the pressure within the mask 4 starts to fall (but is still above the valve's 12 threshold value), for example, when the patient 2 inhales, the piston 18 moves closer to the floating valve seat 22, thereby reducing the volume of gas that is exhausted from the valve 12. By reducing the volume of gas that is exhausted from the valve 12, a fall in pressure within the mask 4 is prevented.

Figure 4:
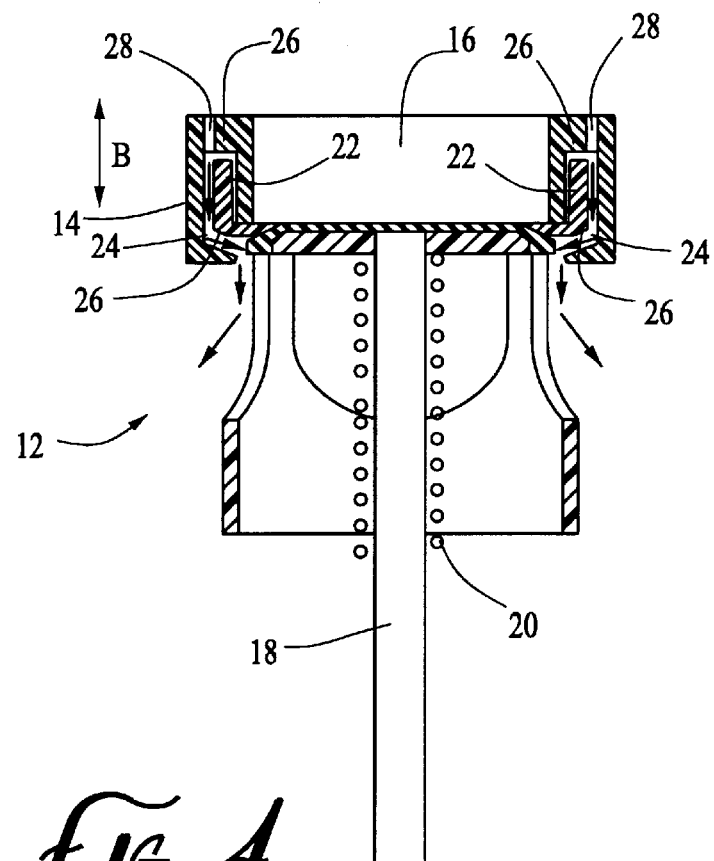
FIG. 4 shows a cross-sectional view of the valve. In this view the pressure from the flow generator is below the threshold pressure of the valve, causing exhausting of gas through a second flowpath.

FIG. 4 illustrates the valve 12 when the pressure falls below the valve's 12 threshold value. In this condition, the gases pushing against the piston 18 cannot overcome the biasing force of the spring 20. Consequently, the piston 18 moves in the direction of arrow C shown in FIG. 2 until the piston 18 engages with the floating valve seat 22. After engaging with the floating valve seat 22, the piston 18 continues to move in the direction of arrow C and pushes the floating valve seat 22 from the first position to a second position (shown in FIG. 4) in which the floating valve seat 22 abuts the valve seat stop 26. When the floating valve seat 22 is in this second position, gas exits the valve 12 via the ports 28 and recessed area 24 as is shown in FIG. 4. The ports 28 and recessed area 24 form a second, alternative exhaust flowpath. Gas does not, however, exit the valve 12 from the valve lumen 16 because a seal is formed between the piston 18 and the floating valve seat 22.

When the floating valve seat 22 is in the second position, gas can be freely exchanged between the atmosphere and the inside of the mask 4 via the ports 28 and the recessed area 24. Particularly important is the fact that exhalation gases from the patient 2 can be quickly vented to the atmosphere. Consequently, there is no risk that high levels of $CO_2$ will build-up in the mask 4. Similarly, if the source of positive airway pressure 8 stops or fails to produce enough airflow, the patient 2 can inhale atmospheric air into the mask 4 via the same pathway (i.e., the recessed area 24 and the ports 28).

Figure 5:
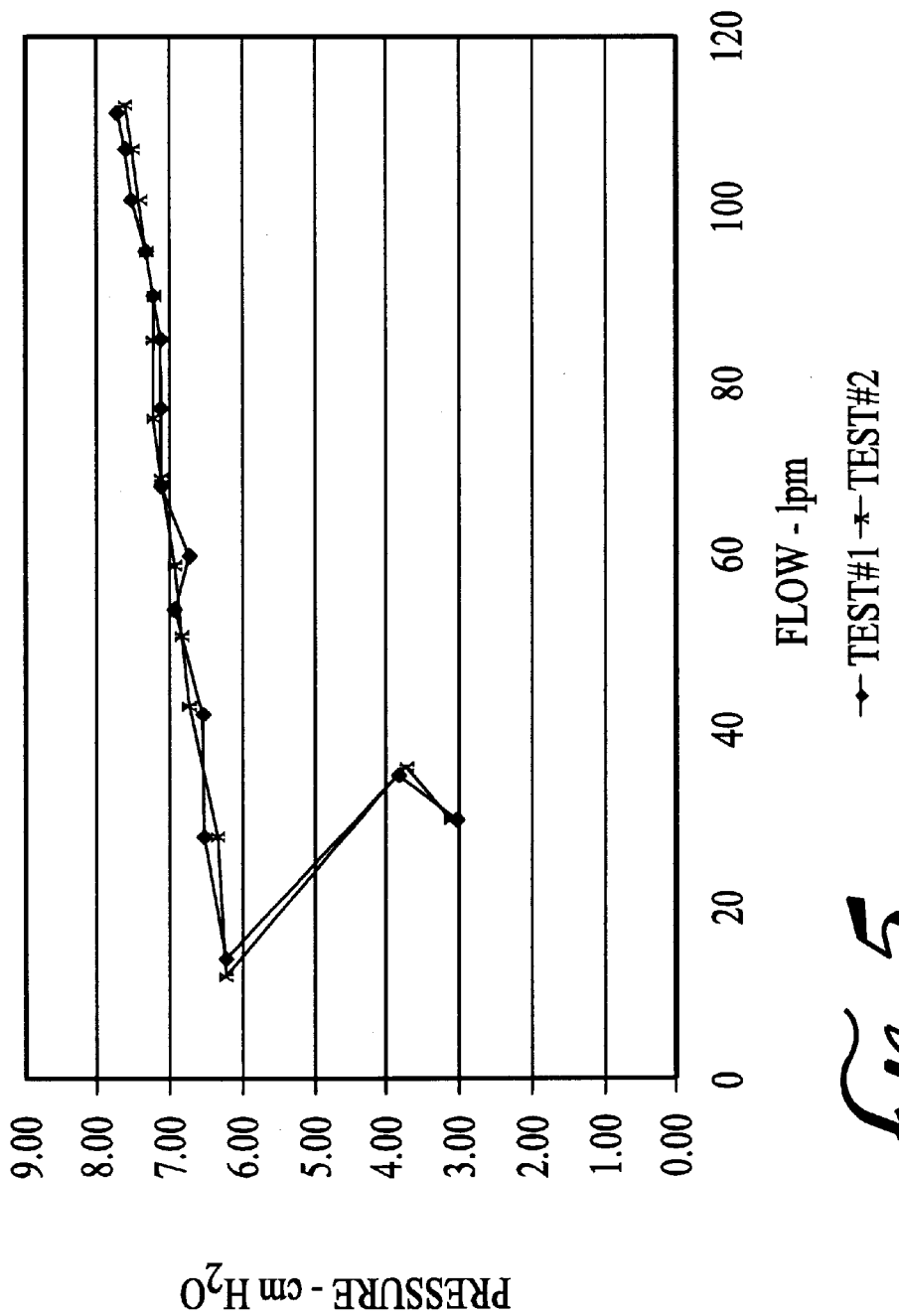
FIG. 5 is a graph illustrating the pressure within a mask employing the valve across a range of flow rates.

FIG. 5 graphically illustrates the ability of the valve 12 to maintain a substantially constant pressure over a wide range of flow rates. The threshold value of the valve 12 used to generate the data is about 6 cm $H_2O$. The valve 12 produces a substantially constant flow rate within the range of about 20 liters/minute to about 100 liters/minute. Within this range, the floating valve seat 22 is in the first position (shown in FIG. 3) and gas is exhausted to the atmosphere from the gap formed between the piston 18 and the floating valve seat 22. When the pressure falls below about 6 cm $H_2O$, the floating valve seat 22 is pushed by the spring-biased piston 18 into the second position, thereby opening an alternative pathway (i.e., through ports 28 and recessed area 24) for gases to flow through.

Preferably, the valve 12 or mask 4 (including valve 12) is prescribed to the patient 2 with a preset threshold value. For example, some patients 2 might be prescribed 10 cm $H_2O$ pressure. For these patients 2, a valve 12/mask 4 preset to 10 cm $H_2O$ is prescribed. Typically, the preset threshold pressure is within the range of about 3 cm $H_2O$ to about 20 cm $H_2O$.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A valve for a continuous positive airway pressure (CPAP) device having a source of positive airway pressure connected to a patient mask, the valve comprising:
   a valve body disposed at or between the patient mask and the source of positive airway pressure, the valve body having a first exhaust flowpath and second exhaust flowpath;
   a floating valve seat disposed in the valve body and moveable between first and second positions;
   a moveable spring-biased piston releasably engaged with the floating valve seat; and
   wherein when the floating valve seat is in the first position, the moveable spring-biased piston is disengaged from valve seat and gas travels out the first exhaust flowpath venting to the atmosphere, and wherein when the floating valve seat is in the second position, the moveable spring-biased piston is engaged with the valve seat and gas travels out the second exhaust flowpath venting to the atmosphere.

2. The valve according to claim 1, wherein the valve is disposed in the patient mask.

3. The valve according to claim 1, wherein floating valve seat moves from the first position to the second position when the pressure produced by the continuous positive airway pressure device drops below a preset pressure.

4. The valve according to claim 3, wherein the preset pressure is within the range of about 3 cm $H_2O$ to about 20 cm $H_2O$.

5. A mask for the delivery of continuous positive airway pressure to a patient comprising:
   a mask, the mask being connectable to a source of positive airway pressure;
   a valve disposed in the mask for controllably releasing gas therefrom to produce a substantially constant pressure inside the mask, the valve comprising:
      a valve body, the valve body having a first exhaust flowpath and second exhaust flowpath;
      a floating valve seat disposed in the valve body and moveable between first and second positions;
      a moveable spring-biased piston releasably engaged with the floating valve seat; and
      wherein when the floating valve seat is in the first position, the moveable spring-biased piston is disengaged from valve seat and gas travels through the first exhaust flowpath venting to the atmosphere, and wherein when the floating valve seat is in the second position, the moveable spring-biased piston in engaged with the valve seat and gas travels through the second exhaust flowpath venting to the atmosphere.

6. The mask according to claim 5, wherein floating valve seat moves from the first position to the second position when the pressure in the mask drops below a preset pressure.

7. The mask of claim 6, wherein the preset pressure is within the range of about 3 cm $H_2O$ to about 20 cm $H_2O$.

8. A valve for maintaining a substantially constant pressure inside a mask used with a continuous positive airway pressure (CPAP) device, the valve comprising:

a body having a first exhaust flowpath and a second exhaust flowpath;

a valve seat disposed in the body and moveable between a first position and a second position depending on the pressure inside the mask; and wherein gas travels out the first exhaust flowpath venting to the atmosphere when the valve seat is in the first position and travels out the second exhaust flowpath venting to the atmosphere when the valve seat is in the second position.

9. The valve in claim 8 further comprising a piston releasably engaged with the valve seat.

10. The valve in claim 9 wherein the piston is spring-biased toward the body of the valve.

11. The valve in claim 8 wherein the body is disposed between the mask and a source of positive airway pressure.

12. The valve in claim 8 wherein the body is disposed at the mask.

13. The valve in claim 8 wherein the valve seat moves from the first second position when the pressure in the mask exceeds a preset pressure.

14. The valve in claim 13 wherein the preset pressure is within the range of about 3 cm $H_2O$ to about 20 cm $H_2O$.

* * * * *